(12) United States Patent
Pouvesle et al.

(10) Patent No.: US 10,420,852 B2
(45) Date of Patent: Sep. 24, 2019

(54) METHOD AND DEVICE FOR GENERATING A PLURALITY OF COLD-PLASMA JETS AT ATMOSPHERIC PRESSURE

(71) Applicants: CENTRE NATIONAL DE LA RECHERCHE SCIENTIFIQUE (CNRS), Paris (FR); UNIVERSITE D'ORLEANS, Orleans (FR); INEL, Artenay (FR)

(72) Inventors: Jean-Michel Pouvesle, Saint-Pryve-Saint-Mesmin (FR); Eric Robert, Orleans (FR); Sebastien Dozias, Saint-Jean de la Ruelle (FR); Michel Hugnot, Orleans (FR); Vanessa Sarron, Cesson-Sevigne (FR); Thibault Darny, Blicourt (FR)

(73) Assignees: CENTRE NATIONAL DE LA RECHERCHE SCIENTIFIQUE (CNRS), Paris (FR); UNIVERSITE D'ORLEANS, Orleans (FR); INEL, Artenay (FR)

( * ) Notice: Subject to any disclaimer, the term of this patent is extended or adjusted under 35 U.S.C. 154(b) by 160 days.

(21) Appl. No.: 15/529,430

(22) PCT Filed: Nov. 26, 2015

(86) PCT No.: PCT/EP2015/077834
§ 371 (c)(1),
(2) Date: May 24, 2017

(87) PCT Pub. No.: WO2016/083539
PCT Pub. Date: Jun. 2, 2016

(65) Prior Publication Data
US 2017/0319727 A1    Nov. 9, 2017

(30) Foreign Application Priority Data
Nov. 26, 2014    (FR) ...................... 14 61511

(51) Int. Cl.
*A61L 2/00* (2006.01)
*B01J 19/08* (2006.01)
(Continued)

(52) U.S. Cl.
CPC ................. *A61L 2/14* (2013.01); *H05H 1/46* (2013.01); *A61L 2202/11* (2013.01);
(Continued)

(58) Field of Classification Search
CPC .... A61B 18/042; H05H 1/24; H01L 2924/00; H01J 37/32642; A61L 2/00; A61L 2/03
(Continued)

(56) References Cited

U.S. PATENT DOCUMENTS 6,406,759 B1    6/2002    Roth
8,267,884 B1 *  9/2012    Hicks .................. A61B 18/042
                                              315/111.21
(Continued)

FOREIGN PATENT DOCUMENTS

WO    WO-0079843    12/2000

OTHER PUBLICATIONS

International Search Report and Written Opinion with English Language Translation, dated Jan. 4, 2016, Application No. PCT/EP2015/077834.

*Primary Examiner* — Monzer R Chorbaji
(74) *Attorney, Agent, or Firm* — Womble Bond Dickinson (US) LLP

(57) ABSTRACT

The invention relates to a method (S) for generating a plurality of cold-plasma jets at atmospheric pressure in order to treat a target (2), wherein said method includes the following steps: producing (S1) a primary cold-plasma jet (3) at atmospheric pressure using a plasma source (10); placing (S2) a substrate (20, 21, 30, 32, 34) near the target (2) to be treated, said substrate (20, 21, 30, 32, 34) including
(Continued)

at least two through-holes; and passing (S3) the plasma through the through-holes (22) of the substrate (20) such as to generate at least two secondary cold-plasma jets (4) at atmospheric pressure.

15 Claims, 7 Drawing Sheets

(51) Int. Cl.
    *A61L 9/00*         (2006.01)
    *A61L 2/14*         (2006.01)
    *H05H 1/46*        (2006.01)

(52) U.S. Cl.
    CPC ............. *H05H 2001/466* (2013.01); *H05H 2001/4645* (2013.01); *H05H 2240/10* (2013.01); *H05H 2240/20* (2013.01); *H05H 2245/1225* (2013.01)

(58) Field of Classification Search
    USPC .................... 422/22, 186.05, 305–306
    See application file for complete search history.

(56) References Cited

U.S. PATENT DOCUMENTS

| | | |
|---|---|---|
| 2002/0187066 A1 | 12/2002 | Yu et al. |
| 2013/0272929 A1 | 10/2013 | Pelfrey et al. |
| 2014/0069459 A1* | 3/2014 | Guan .................. H05H 1/24 134/1.1 |

* cited by examiner

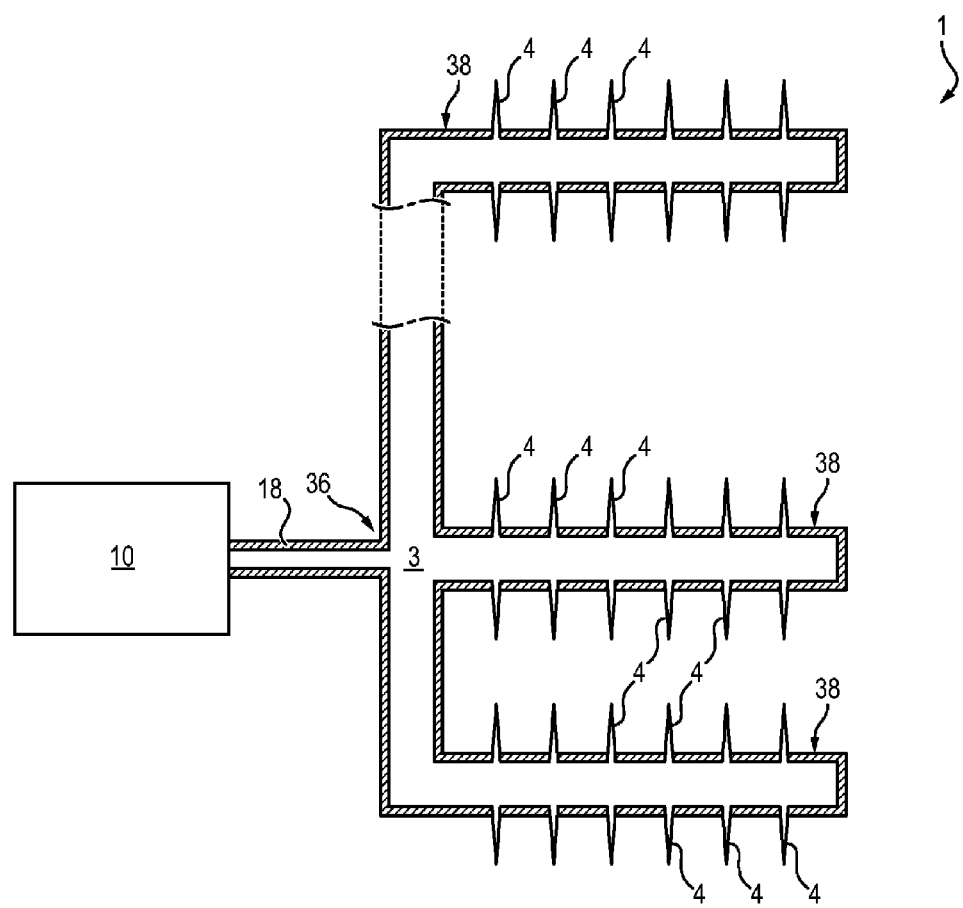

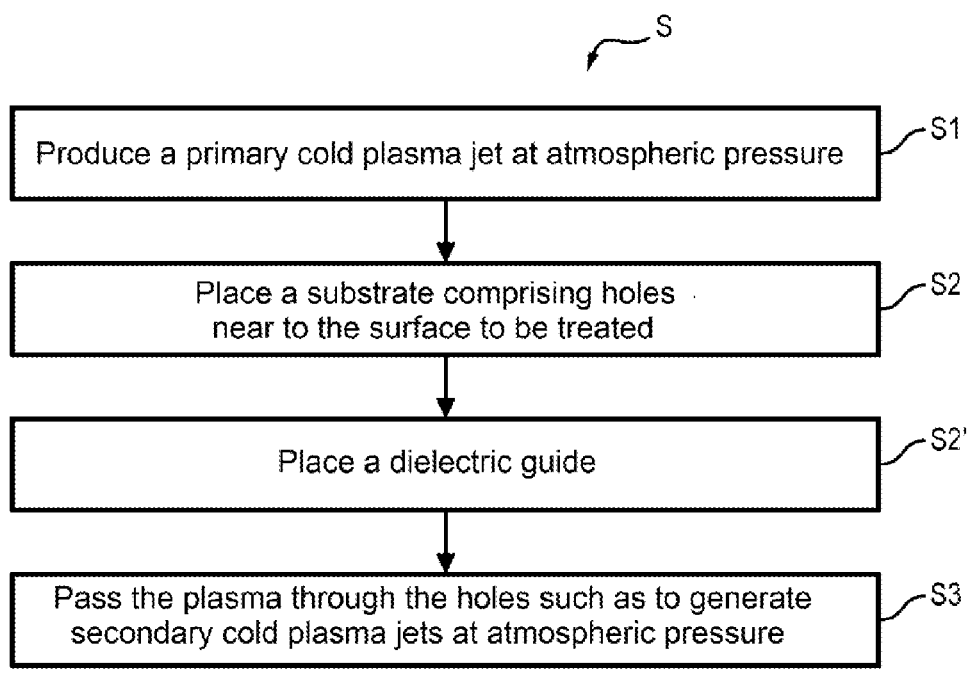

METHOD AND DEVICE FOR GENERATING A PLURALITY OF COLD-PLASMA JETS AT ATMOSPHERIC PRESSURE

FIELD OF THE INVENTION

The invention relates to a device allowing simultaneous or sequential generation of a plurality of plasma jets, in particular cold plasma jets at atmospheric pressure.

The invention finds application in particular in the following fields: the biomedical field, sterilization, medicine, cosmetics, material treatment, functionalizing surfaces, decontamination, germination, lighting, rapid commutation, flow modification, detection or metrology.

TECHNOLOGICAL BACKGROUND

A plasma is a material phase comprising charged particles, ions and electrons. Typically, it consists of an ionized gas, that is a gas comprising free electrons which are not linked to an atom or a molecule. Free electrons make the plasma a conductor of electricity.

The invention relates more particularly to cold plasmas at atmospheric pressure.

Currently, the production of cold plasma jets at atmospheric pressure is the subject of much research, taking into consideration the increasing importance of their application in numerous and varied fields, such as biomedical, medicine, sterilization, decontamination and material treatment.

These cold plasma jets have, however, the disadvantage of only allowing small surfaces to be processed, due to the small dimension of the jets which can currently be produced.

It has therefore been proposed to implement scanning systems so as to scan the surfaces to be treated using the cold plasma jet produced according to conventional techniques. Scanning, however, requires the implementation of a system capable of setting the plasma jet into motion over the surface to be treated, which makes the device relatively complex and increases its bulk considerably.

It has also been proposed to couple a large number of plasma jets from multi-electrode and multi-generator systems. Thus, in order to obtain n plasma jets, this solution proposes to associate n electrodes with an equal number of generators. Such a coupling does in fact make it possible to increase the surface area of the zone to be treated by multiplying the plasma jet sources. However, in order for the plasma jets not to interfere, it is necessary to separate the discharge electrodes. Moreover, this solution is relatively expensive, bulky and complex to implement due to the multiplication of discharge electrodes and/or of capillaries and gas supply pipes.

Current technology definitely allows a reduction in the size of the plasma sources (see microcavity devices in particular—IEEE TRANSACTIONS ON PLASMA SCIENCE, Vol. 41, No. 4, April 2013). This miniaturization, however, has a non-negligible cost and is very complex to implement. It also does not allow the generation of plasmas of large dimensions, or on the contrary sufficiently small to treat targets having at least one very small dimension and a large aspect ratio, such as endoscopic systems.

SUMMARY OF THE INVENTION

One aim of the invention is therefore to propose a new device and an associated method making it possible to generate a cold plasma at atmospheric pressure by reducing the number of sources necessary for generating the plasma, which in addition is capable of producing plasmas capable of treating any type of target, independently of its dimensions and aspect ratio, as well as targets comprising a dielectric or conductive material.

To this end, the invention proposes a method for generating a plurality of cold plasma jets at atmospheric pressure in order to treat a target, comprising the following steps:

producing a primary cold plasma jet at atmospheric pressure using a plasma source, placing a substrate near the target to be treated, said substrate comprising at least two through holes, passing the primary plasma jet through the through holes such as to generate at least two secondary cold plasma jets at atmospheric pressure.

Certain preferred but not limiting features of the generation method described above are the following:

the primary plasma jet is produced by generating electrical discharges in a flow of plasmagene gas, the method also comprises a step during which a guide formed in a dielectric material is placed between the plasma source and the substrate, so as to transport the gas flow toward the through holes of said substrate, an aspect ratio of the through holes of the substrate is comprised between 1 and 100, preferably between 5 and 50, the flow rate of the gas flow entering into the plasma source is comprised between one or more standard cubic centimeters per minute and a few standard liters per minute, the plasmagene gas flow comprises a rare gas, a mixture of rare gases or a mixture of one or more rare gases with minority mixture comprising one or more molecular gases, and the target to be treated comprises a hollow structure, the method comprising a sub-stem consisting of the introduction of the substrate into said hollow structure prior to the step consisting of passing the primary plasma jet through the through holes.

According to a second aspect, the invention also proposes a device for generating a plurality of cold plasma jets at atmospheric pressure in order to treat a target, the device comprising:

a plasma source, configured to produce a primary cold plasma jet at atmospheric pressure, a substrate comprising a plurality of through holes, and means configured to pass the primary plasma jet through the through holes of the substrate such as to generate a plurality of secondary cold plasma jets at atmospheric pressure.

Certain preferred but not limiting features of the device described above are the following:

the substrate is formed of one of the following materials: a dielectric material, a conductive material, a conductive material covered with a target of a dielectric material, a dielectric material covered at its surface with a conductive material, or comprising a first portion formed with a dielectric material and a second portion formed with a conductive material, the substrate comprises an sleeve comprising a first end 21a) configured to receive the plasma and a second end opposite the first end, the through holes being distributed over a surface of the sleeve or being aligned between the first and the second end of the sleeve, the substrate comprises a flat substrate, extending substantially perpendicular to a propagation direction of the primary plasma jet, the through holes being formed in one surface of said flat substrate; a substrate having a surface of cylindrical shape, comprising a series of through holes formed in the surface of the sleeve and configured to form as many secondary plasma jets; an sleeve having a surface of cylindrical shape comprising two series of holes extending in the same plane between the first and the second end of the sleeve and configured to form two lines of secondary plasma jets extending radially from the sleeve; a tube having a substantially cylindrical surface of revolution wherein are formed a plurality of lines of through holes configured to form a plurality of lines of secondary plasma jets; an internal tube accommodated in an external tube, one of the internal tube and the external tube being substantially continuous while the through holes are formed in the other of the external tube and the internal tube; and/or a brush having a surface shaped substantially as a cylinder of revolution and comprising a plurality of through holes distributed on its surface, the substrate comprises several branches connected together at a core, said core being adjacent to the plasma source, the device further comprises a guide formed in a dielectric material extending between the plasma source and the substrate, so as to transport the flow of gas toward the through holes of said substrate, the device further comprises an intermediate guide, positioned between the plasma source and the guide formed in a dielectric material, the guide formed in a dielectric material being connected to a source of plasmagene gas and to the substrate, and the intermediate guide is conductive and connected to an electrode of the plasma source so as to form the primary plasma jet, said primary plasma jet being then transferred to the guide formed in a dielectric material.

BRIEF DESCRIPTION OF THE DRAWINGS

Other features, aims and advantages of the present invention will appear more clearly upon reading the detailed description which follows, and with reference to the appended drawings given by way of non-limiting examples wherein:

FIGS. 3a to 3h illustrate other embodiments of a substrate which can be used in the device of FIG. 1.

FIG. 4 is a flowchart showing different steps of a method of generating a plurality of cold plasma jets at atmospheric pressure conforming to the invention.

DETAILED DESCRIPTION OF AN EMBODIMENT

Figure 1:
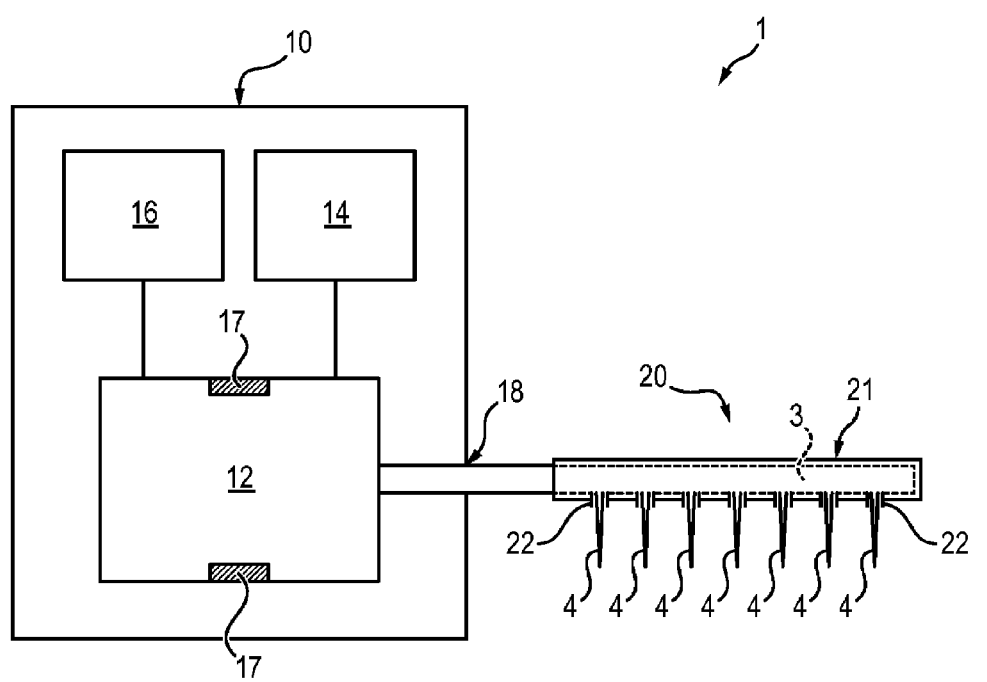
FIG. 1 is a schematic of an embodiment of a device for generating a plurality of cold plasma jets at atmospheric pressure conforming to the invention.

A method S and a device 1 for generating a plurality of cold plasma jets at atmospheric pressure in order to treat a target 2 conforming to the invention will now be described with reference to the appended drawings. The target 2 can in particular comprise physical matter, living tissue or a volume of fluid, and can if applicable be placed on a grounded support so as to modify the quality of the plasma and vary the reactive species and the electric field which have an impact on the target 2.

The term cold plasma at atmospheric pressure will be understood hereafter to mean a gaseous plasma not in thermal equilibrium for which the temperature of the electrons is very high with respect to the temperature of the other species contained within the plasma, the latter temperature remaining near ambient temperature.

Thus, the invention is not limited in its application to ambient temperature or ambient pressure. In particular, the invention applies, mutatis mutandis to the generation of cold plasma jets at a pressure extending from a hundred torr (10 kPa) to several atmospheres (i.e. several hundred kPa) and/or to low temperatures (that is preferably less than a hundred degrees Celsius).

It will be noted however that the temperature of the method S of the invention can be limited by the type of target 2 to be treated: typically, for biological materials, the temperature is preferably less than forty degrees Celsius.

During a first step S1, the method S comprises the production of a cold plasma jet at atmospheric pressure by means of a plasma source 10.

Hereafter, the plasma jet obtained by the plasma source 10 will be designated by the terminology "primary plasma jet 3."

The cold plasma source 10 can in particular conform to the plasma generation device described in document WO 2009/050240. However, any device 1 capable of delivering a cold plasma jet at atmospheric pressure can be used as the plasma source 10.

Thus, the plasma source 10 can for example comprise an enclosure 12, connected to a plasma gas source 14, wherein are accommodated at least one electrode, for example two electrodes 17 connected to a high voltage generator 16.

The plasma gas source 14 can in particular comprise a source 14 for a rare gas, a mixture of rare gases (typically helium He, argon Ar, etc) or a mixture of one or more rare gases with one or more molecular gases (typically oxygen $O_2$, hydrogen $H_2$, sulfur hexafluoride $SF_6$, nitrogen $N_2$ and water vapor $H_2O$ etc.) as minorities, that is added in low concentrations.

The generator 16 is preferably configured to apply an electrical discharge having a very rapid voltage peak (typically less than a few microseconds) between zero and several tens of kilovolts, so as to create a very rapid ionization front within the plasmagene gas. Moreover, the generator 16 can apply alternating current at various frequencies ranging from fifty hertz to several kilohertz. As a variant, the generator 16 can apply impulsive current and generate single or repeated discharges at very high frequency (extending to a hundred kilohertz). In this variant embodiment, the electrodes 17 can be supplied with either positive or negative polarity.

In this manner, the application in the enclosure 12 of an electrical discharge by the electrodes 17 in the plasmagene gas flow has the effect of producing a primary plasma jet 3.

The primary plasma jet 3 is then directed toward an outlet of the enclosure 12.

Optionally, a guide 18 made of a dielectric material can be placed at the outlet of the enclosure 12 so as to bring the primary plasma jet 3 into the region situated at a distance from the plasma source 10. In this embodiment, the guide 18 contains a gas or a mixture of gases allowing the transport of the primary plasma jet to the desired region, which can be placed at a distance extending from a few millimeters to several centimeters or several meters from the plasma source 10, depending on need. The guide 18 can in particular have the shape of a cylindrical or tubular sleeve. The gas or the mixture of gases contained in the guide 18 can be selected among the plasmagene gases likely to be created by the source 14. This gas contained in the guide 18 can be different from that created by the source 14 and constitutes an additional contribution.

Figure 3A:
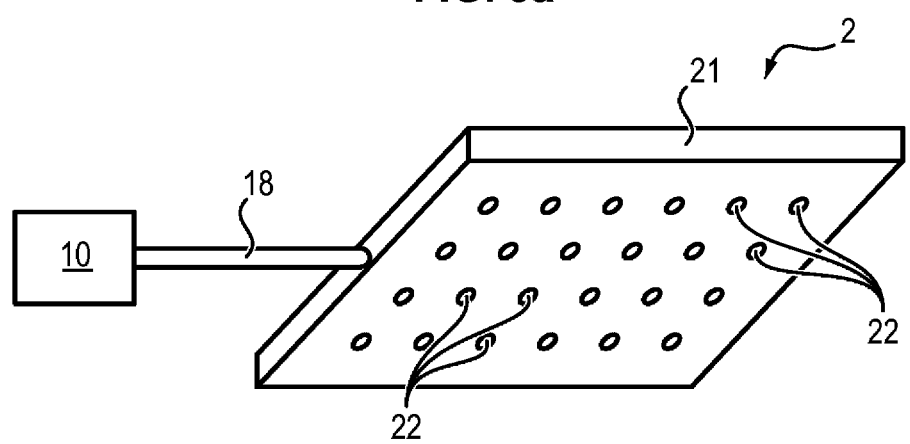
Figure 3B:
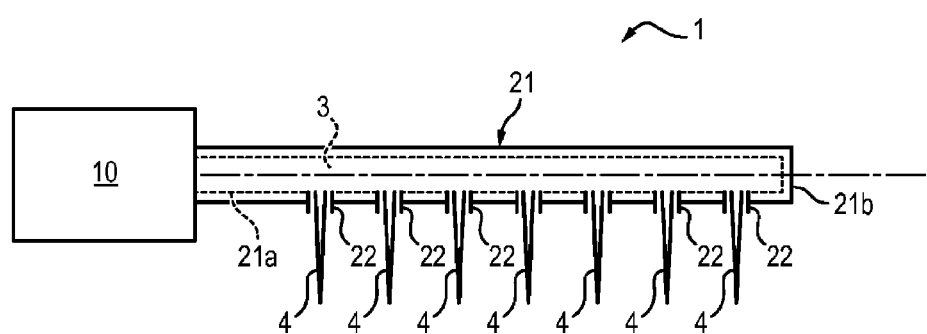
Figure 3C:
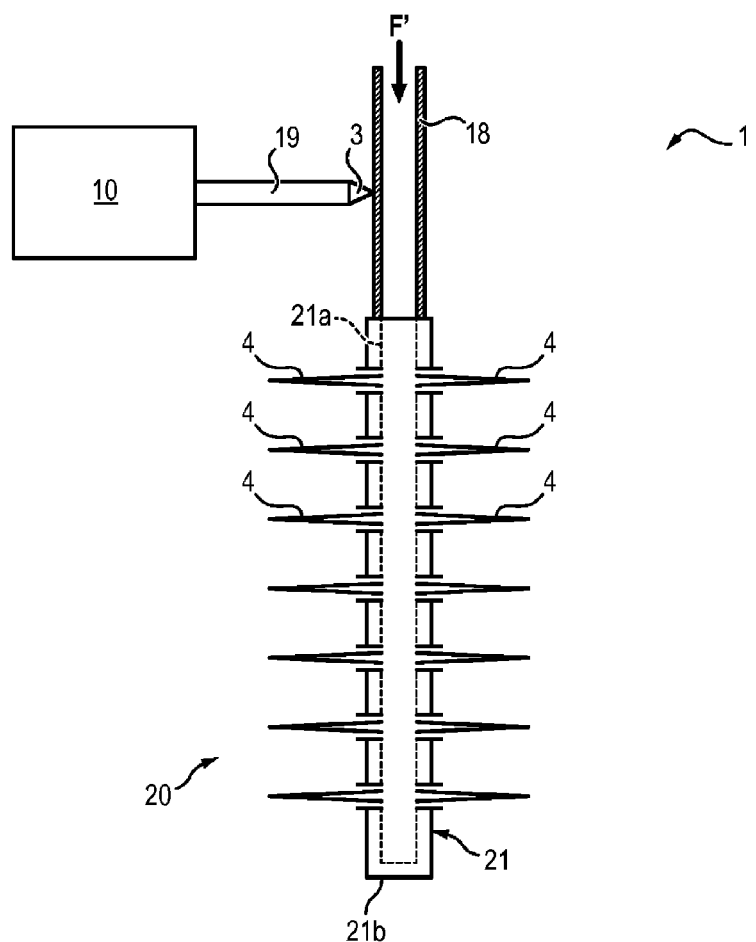

In a variant embodiment illustrated in FIG. 3c, the plasma source 10 can be placed in fluid communication with the dielectric guide 18 through an intermediate guide 19. The intermediate guide 19 can then be dielectric, conductor or dielectric and comprising a conductive insert.

For this purpose, the plasma source 10 can inject a cold plasma jet at atmospheric pressure into the intermediate guide 19, which then forms a primary plasma jet 3 at its free end which is transferred into the dielectric guide 18. Moreover, a plasmagene gas flow source F' is put into fluid communication with the dielectric guide 18 to inject the flow F' into a first end of the dielectric guide 18, while the second end of the dielectric guide 18 is connected to the substrate 20. In this manner, the primary plasma jet 3 leaving the intermediate guide 19 is transported by the dielectric guide 18 to the substrate 20, where the different plasma jets 4 are produced.

Alternatively, when the intermediate guide 19 is made of a conductive material, it can be connected directly to one of the electrodes 17. The primary plasma jet 3 is then formed at the end of the intermediate conductor 19, then transferred into the dielectric guide 18 wherein the plasmagene gas flow F' leaving the source 14 circulates so as to produce the plasma jets 4.

During a second step S2, a substrate 20 is placed near the target 2 to be treated.

The substrate 20 is configured to form, based on the primary plasma jet 3 produced by the source, at least two plasma jets 4, preferably a plurality of plasma jets 4.

To this end, the substrate 20 comprises at least two through holes 22, preferably as many through holes 22 as there are plasma jets 4 to be produced. The through holes 22 make it possible to put into fluid communication the plasma source 10 with the target 2 to be treated.

If required, a guide 18 formed of a dielectric material can be placed between the plasma source 10 and the substrate 20, so as to transport the gas flow toward the through holes 22 of the substrate 20 (step S2').

It will of course be understood that the first and the second step S1, S2 can be inverted, as it is possible to place the substrate 20 near the target 2 to be treated prior to the production of the primary plasma jet 3 by the plasma source 10.

During a third step S3, the primary plasma jet 3a is then made to pass through the through holes 22 such as to generate at least two cold plasma jets 4 at atmospheric pressure, preferably a plurality of plasma jets 4.

More precisely, the primary plasma jet 3 is applied to the substrate 20, so as to pass through the different through holes 22 which are formed in the substrate 20 and thus generate the different plasma jets 4.

Hereafter, plasma jets 4 formed by passage of the primary plasma jet 4 formed by passage of the primary plasma jet 3 in the through holes 22 of the substrate 20 will be designated by the terminology "secondary plasma jets 4."

The invention then makes possible, using a single generator 16 and a single source of plasma gas 14, to obtain a plurality of secondary plasma jets 4. The device 1 of the invention is therefore less complex and less expensive to manufacture than conventional multi-electrode systems and multi-generator systems. In fact, a single generator 16 makes it possible to produce, thanks to the substrate 20, several hundred secondary plasma jets 4.

The device 1 of the invention also makes it possible to reduce drastically the consumption of plasmagene gas for creating a large number of secondary plasma jets 4. For example, a entering flow of plasmagene gas on the order of a liter per minute suffices to produce a hundred secondary plasma jets 4, while the multi-electrode and multi-generator system of the prior art require a liter per minute of plasmagene gas per jet of plasma produced (which comes to approximately 100 liters per minute of plasmagene gas for the production of a hundred plasma jets produced).

The shape, the dimensions and the material constituting the substrate 20 depend on the type of target 2 to be treated.

The substrate 20 can in particular be made of a dielectric material (sequential mode), a conductive material (simultaneous mode), a conductive material covered on the surface with a dielectric material, a dielectric material covered on its surface with a conductive material, or a first portion formed of a dielectric material and a second portion formed of a conductive material.

The implementation of an electrically conductive material, such as a metallic material, makes it possible to produce more secondary plasma jets 4 substantially identical to one another (that is to say homogeneous), the metallic material being capable of conducting electrons coming from the primary plasma jet 3. Such a material, however, is not adapted to all types of application. In particular, a substrate 20 made of a conductive material can only be implemented if the target 2 to be treated allows it (taking into consideration the high voltages which are applied by the generator 16). This type of material can for example be favored for the creation of secondary plasma jets 4 on an industrial scale, when the target 2 to be treated allows it.

On the other hand, the implementation of a dielectric material makes it possible to implement the invention regardless of the type of target 2 to be treated. This type of material can in particular be favored for biological and medical applications, or for objects considered fragile. For example, the dielectric material can comprise a ceramic, glass, plastic or any dielectric material capable of being machined and/or molded into desired shapes and dimensions for the substrate 20.

The implementation of a substrate 20 formed in a conductive material covered at its surface with a dielectric material has the advantage of easily producing homogeneous jets of secondary plasma 4 regardless of the target 2 to be treated. This type of substrate 20 is, however, more complex to create than exclusively dielectric or electrically conductive substrates 20.

Targets 2 which can be treated with the device 1 and the method S of the invention can therefore be of a very different nature; only the material constituting the substrate 20 needing to be adapted (electrically conductive material and/or dielectric) to the type of target 2 to be treated. The targets 2 which can be treated can therefore also comprise inert dielectric or conductive materials, biological tissues, organs, etc. It is even possible to treat liquids at their surface or, as a variant, by immersing the substrate 20 directly in these liquids.

Moreover, the targets 2 which can be treated can have various shapes and dimensions (from a few millimeters to a few meters), in two dimensions or in three dimensions.

In fact, any type of target 2 can also be treated, no matter what the aspect ratio (including targets 2 comprising one very small dimension compared with the other dimensions, such as pipes and catheters for example) or the dimensions of the target 2. It is sufficient in fact to adapt the dimensions and the shape of the substrate 20 to the dimensions and the shape of the target 2 to be treated.

The substrate 20 can in fact have diverse and varied shapes depending on the type of application required. In particular the shape of the substrate 20 and the distribution of holes 22 can be selected so as to obtain a plasma fountain, a plasma shower, a plasma curtain, a plasma layer or even a plasma sprinkler, simply and at low cost, the substrate 20 also being able to have a two-dimensional or three-dimensional shape.

Figure 2:
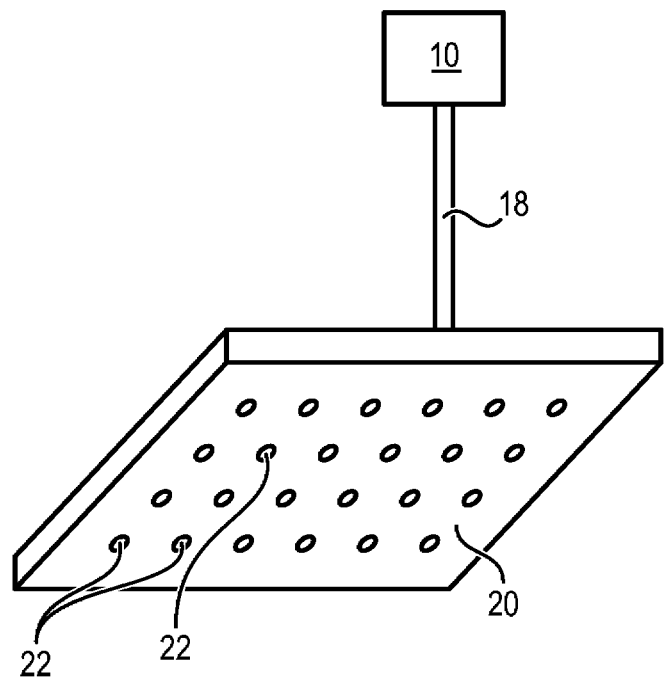
FIG. 2 illustrates a first embodiment of a substrate which can be used in the device of FIG. 1.

For example, the substrate 20 can be flat and extend substantially perpendicular to the direction of flow of the primary plasma jet 3 (FIG. 2).

As a variant, the substrate 20 can comprise an sleeve 21 forming a guide having a first end 21a configured to receive the primary plasma jet 3 and a second end 21b which is opposite to the first end 21a and can be open or closed. In this variant embodiment, the primary plasma jet 3 moves between the first and the second end 21a, 21b of the sleeve 21 and produces secondary plasma jets 4 by passing through through-holes 22 which extend between these two ends 21a, 21b.

Examples of sleeves 21 have been illustrated in FIGS. 3a to 3g.

FIGS. 3a and 3b illustrate an example of a sleeve 21 of cylindrical shape comprising a series of through holes 22 aligned along the sleeve 21, between its first and its second end 21b, configured to form a series of secondary plasma jets 4. Here the second end 21b of the sleeve 21 is closed.

In the case of FIG. 3a, the sleeve 21 has a substantially rectangular shape and comprises two opposite flat faces interconnected by at least three sides, between which circulates the primary plasma jet 3. The primary plasma jet 3 is introduced here by a hole formed in one of the sides of the sleeve 12, the dimensions of the hole being substantially smaller than the length of the sides of the envelope 21. This exemplary embodiment thus makes it possible to obtain a matrix of secondary plasma jets 4.

In the case of FIG. 3b, the sleeve 21 has a cylinder of revolution shape and the through holes 22 are aligned along a line which extends between the two ends 21a, 21b of the sleeve 21. This exemplary embodiment thus makes it possible to obtain a line of secondary plasma jets 4.

FIG. 3c illustrates an example of a sleeve 21 with a cylindrical shape comprising two series of aligned holes 22 extending in the same plane along the envelope 21, between the two ends 21a, 21b. This exemplary embodiment therefore makes it possible to obtain two lines of secondary plasma jets 4, propagating radially from the sleeve 21 in the same plane. Here too, the second end 21b of the sleeve 21 is closed.

This example is not limiting, however, the series of holes being able to extend in different planes.

In this exemplary embodiment, the plasma source 10 is put into fluid communication with the dielectric guide 18 via the intermediate guide 19. More precisely, the primary plasma jet 3 is transferred by the intermediate guide 19 into the dielectric guide 18 then into the sleeve 21, where the different plasma jets 4 are produced. It will of course be understood that this configuration of the device 1 (with an intermediate guide 19) is not limited to the substrate 20 illustrated in FIG. 3c, and can be applied to any form of substrate 20.

Figure 3D:
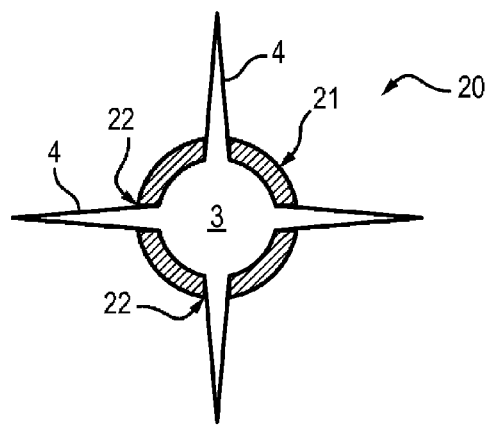

FIG. 3d illustrates an example of a sleeve 21 comprising a tube with a substantially cylindrical-of-revolution shape wherein are formed several lines of through holes 22, four lines here. This exemplary embodiment therefore makes it possible to obtain several lines of plasma jets 4 extending radially with respect to the sleeve 21, here four lines forming a cross.

Figure 3E:
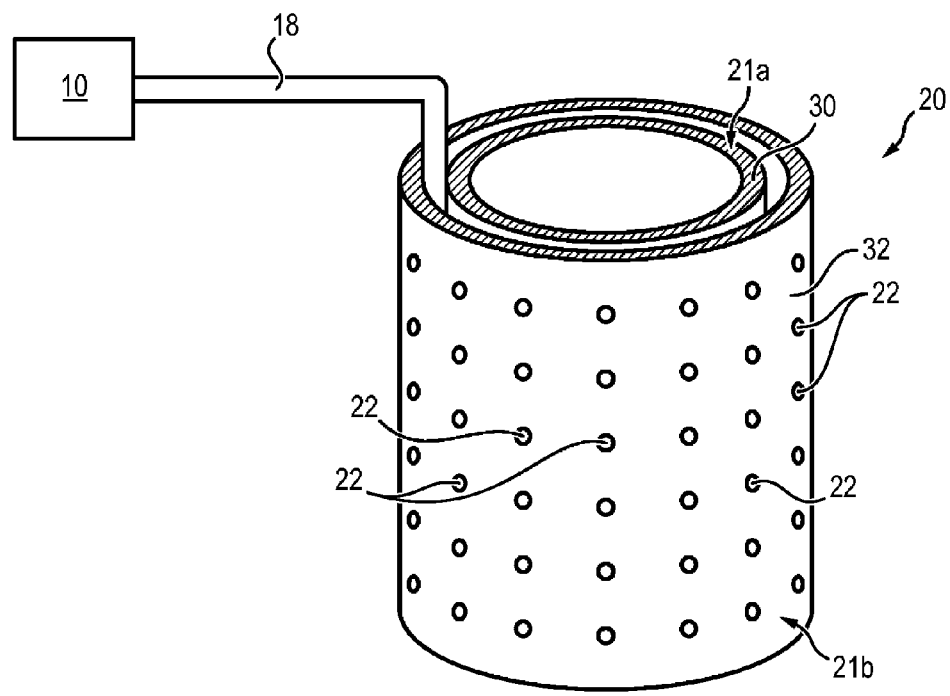
Figure 3F:
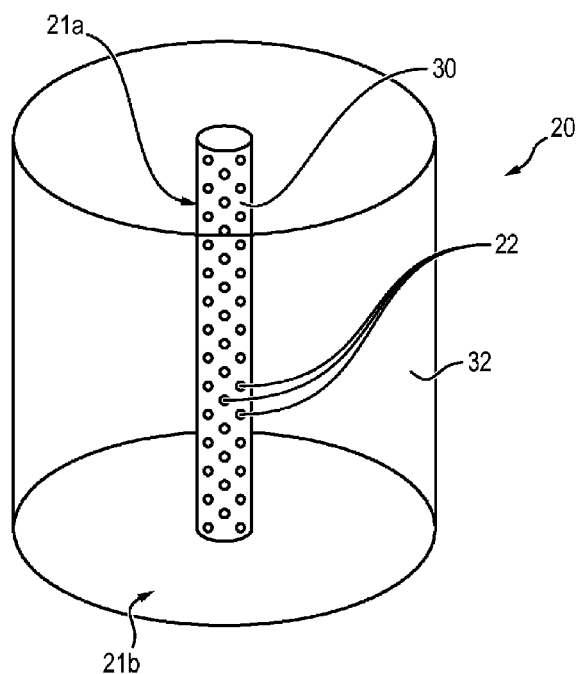

FIG. 3e illustrates an example of a sleeve 21, comprising a substantially continuous internal (that is without through holes 22) tube 30 accommodated in an external tube 32 wherein are formed a plurality of through holes 22. Here the internal tube 30 and the external tube 32 are cylinders of revolution and coaxial. In this exemplary embodiment, the introduction of a primary plasma jet 3 into the internal tube 30 and the external tube 32 therefore makes it possible to obtain a plurality of secondary plasma jets 4 extending radially from the external tube 32, between the first and the second end 21a, 21b.

As a variant (see FIG. 3f), the through holes 22 can be formed in the internal tube 30 instead of the external tube 32 of the sleeve 21. This variant embodiment make it possible in particular to project the secondary plasma jets 4 thus produced into a confined space so as to obtain a diffused plasma.

Figure 3G:
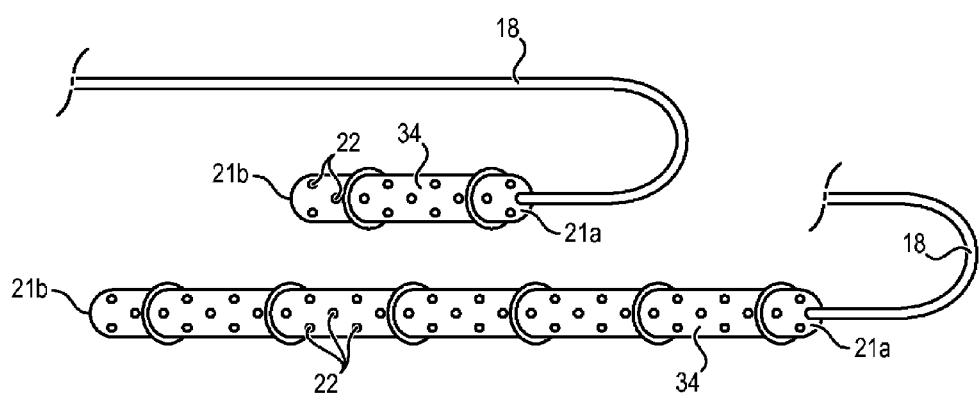

FIG. 3g illustrates two exemplary embodiments wherein the sleeve 21 has the shape of a brush 34 having a substantially cylinder-of-revolution shape and comprising a plurality of through holes 22 distributed over its target 2 between its first and its second end 21b. If necessary, the second end 21b can be closed. Optionally, the brush 34 can be connected to a flexible dielectric guide 18 at its first end 21a so as to facilitate its handling.

Typically, a brush 34 can be implemented for the treatment of an internal surface of a target 2 having a hollow structure, even if this hollow structure has a high aspect ratio, as is the case for example in a catheter or an endoscopic device. It is sufficient, in fact, to create a brush 34 with dimensions adapted to enter the catheter or the endoscopic device to be treated.

Optionally, the brushes 34 can comprise rings attached to the external surface of the sleeve 21, substantially coaxial with the sleeve 21. The rings make it possible to improve the circulation of the secondary plasma jets when the brush is introduced into the hollow structure of the target.

The device 1 and the method S of the invention therefore make it possible to treat the target 2 of an object having a very high aspect ratio with one dimension on the order of a few micrometers, such as a catheter. By comparison, conventional cold plasma jet production techniques are not capable of treating such targets 2, in that they cannot sufficiently control the dimensions or the shape of the jets thus produced to be able to introduce them into such an object.

FIG. 3h illustrates an exemplary embodiment wherein the dielectric guide 18 comprises several branches 38 connected together at a central core 36. It is then the central core 36 which is placed in proximity to the plasma source 10 and distributes the primary plasma jet 3 into the different branches 38. Here, each branch 38 can comprise a sleeve 21 conforming to the exemplary embodiments illustrated in FIGS. 3a through 3g.

Moreover, the through holes 33 of the same substrate 20 can have different shapes and dimensions. Typically, the through holes 22 can be of an overall circular, oval, parallelepiped, etc. shape.

Naturally, whatever the form of the embodiment, a sleeve 21 comprising a different number of lines of holes 22, or holes 22 distributed according to a different distribution matrix (random distribution, alternating, etc.) than that described in relation with the appended figures can equally well be implemented for creating secondary plasma jets 4.

The position, the diameter and the depth of the through holes 22 can moreover be selected depending on the desired application and/or the flow rate of plasmagene gas entering the plasma source 10.

Typically, the diameter of the holes 22 can be comprised between several micrometers (for example in the case of the nano-functionalization of a target 2) and several millimeters (for example in the case of a dermatological treatment of biological tissues).

Depending on the applications, it may also be preferable to obtain secondary plasma jets 4 which do not interfere with one another (that is to say without electromagnetic interaction).

Given that the plasma source 10 produces discontinuous secondary plasma jets 4 which each have a high propagation speed (typically on the order of some $10^3$ to $10^6$ meters per second ($m \cdot s^{-1}$)), a judicious selection of the distance between two adjacent through holes 22, of their shape and their respective depths depending on the flow rate of the plasmagene gas flor makes it possible to avoid electrostatic interactions between the secondary plasma jets 4 produced by these two adjacent through holes 22. In fact, the greater the distance traveled by the primary plasma jet 3 between the formation of two secondary plasma jets 4, the fewer risks there are of electrostatic interaction. However, this distance traveled can in particular be adjusted depending on the distance between the adjacent through holes 22 and/or the depth of the through holes 22 (which depends on the thickness of the substrate 20), according to the flow of plasmagene gas entering the plasma source 10.

In this manner, the secondary plasma jet 4 can be produced by the through opening 22 closest to the plasma source 10 before the next secondary plasma jet 4 is formed.

The Applicants became aware that, depending on the flow rate of gas entering the plasma source 10, the judicious selection of the aspect ratio (length over diameter) of the through holes 22 of the substrate 20 influenced the volume of gas leaving said holes 22 thus allowing limitation of the risks of interaction between the two adjacent secondary plasma jets 4. The aspect ratio of the holes 22 can in particular be comprised between 1 and 100.

For example, the holes 22 can have an aspect ratio comprised between 5 and 50 when the flow rate of the gas flow entering the plasma source 10 is comprised between one and several standard cubic centimeters per minute (sccm) and a few standard liters per minute (sLm)(under the reference conditions of 20° C. and 1013 $10^2$ Pa).

The different secondary plasma jets 4 obtained by means of the same substrate 20 therefore form, not simultaneously but successively depending on the propagation speed of the primary plasma jet 3 produced by the plasma source 10 and the position and the dimensions of the through holes 22.

This discontinuity in the formation of secondary plasma jets 4 by means of the substrate 20 has no influence, however, on the treatment of the target 2, the interval between the formation of two adjacent secondary plasma jets 4 being on the order of a few nanoseconds to a few microseconds. The treatment of the target 2 by means of secondary plasma jets 4 obtained using the method S of the invention is therefore homogeneous.

The device 1 and the method S of the invention therefore make it possible to generate secondary plasma jets 4 of different lengths, extending from several tens of micrometers to several centimeters, in a controlled manner thanks to the substrate 20.

The invention claimed is:

1. A method for generating a plurality of cold plasma jets at atmospheric pressure in order to treat a target, comprising the following steps:
    producing a primary cold plasma jet at atmospheric pressure using a plasma source,
    placing a substrate near the target to be treated, said substrate comprising at least two through holes,
    passing the primary plasma jet through the through holes such as to generate at least two secondary cold plasma jets at atmospheric pressure, and
    wherein the flow rate of the gas flow entering the plasma source is comprised between one and several standard cubic centimeters per minute and a few standard liters per minute.

2. The generation method according to claim 1, wherein the primary plasma jet is produced by generating electrical discharges in a flow of plasmagene gas.

3. The generation method according to claim 2, further comprising a step wherein a guide formed of a dielectric material is placed between the plasma source and the substrate, so as to transport the gas flow toward the through holes of said substrate.

4. The generation method according to claim 2, wherein an aspect ratio of the through holes of the substrate is comprised between 1 and 100.

5. The generation method according to claim 2, wherein the flow of plasmagene gas comprises a rare gas, a mixture of rare gases or a mixture of one or more rare gases with a minority admixture comprising one or more molecular gases.

6. The generation method according to claim 2, wherein an aspect ratio of the through holes of the substrate is comprised between 5 and 50.

7. The generation method according to claim 1, wherein the target to be treated comprises a hollow structure, the method comprising a sub-step wherein the substrate is introduced into said hollow structure prior to step of passing the primary plasma jet through the through holes.

8. A device for generating a plurality of cold plasma jets at atmospheric pressure in order to treat a target, the device comprising:
    a plasma source, configured to produce a primary cold plasma jet at atmospheric pressure,
    a substrate comprising a plurality of through holes, and
    means configured to pass the plasma through the through holes of the substrate such as to generate a plurality of secondary cold plasma jets at atmospheric pressure.

9. The generation device according to claim 8, wherein the substrate is formed from one of the following materials: a dielectric material, a conductive material, a conductive material covered by a target of a dielectric material, a dielectric material covered at its surface by a conductive material, or comprises a first portion formed of a dielectric material and a second portion formed in a conductive material.

10. The generation device according to claim 8, wherein the substrate comprises a sleeve comprising a first end configured to receive the plasma and a second end opposite the first end, the through holes being distributed over a surface of the sleeve or being aligned between the first and the second end of the sleeve.

11. The generation device according to claim 10, wherein the substrate comprises:
    a flat substrate, extending substantially perpendicular to a propagation direction of the primary plasma jet, the through holes being formed in a surface of said flat substrate,
    a generation substrate having a surface with a cylindrical shape comprising a series of through holes formed in the surface of the sleeve and configured to form as many secondary plasma jets, a sleeve having a surface with a cylindrical shape comprising two series of holes extending in one plane between the first and the second end of the sleeve and configured to form two lines of secondary plasma jets extending radially from the sleeve, a tube having a substantially cylinder-of-revolution shape wherein are formed a plurality of lines of through holes configured to form a plurality of lines of secondary plasma jets, an internal tube housed in an external tube, one of the internal tube and the external tube being substantially continuous while the through holes are formed in the other of the external tube and the internal tube, or a brush, have a surface with a substantially cylinder-of-revolution shape and comprising a plurality of through holes distributed on its surface.

12. The generation device according to claim 8, wherein the substrate comprises several branches connected together at a core, said core being adjacent to plasma source.

13. The generation device according to claim 8, further comprising a guide formed in a dielectric material extending between the plasma source and the substrate, so as to transport the gas flow toward the through holes of said substrate.

14. The generation device according to claim 13, further comprising an intermediate guide positioned between the plasma source and the guide formed of a dielectric material, the guide formed of a dielectric material being connected to a plasmagene gas source and to the substrate.

15. The generation device according to claim 14, wherein the intermediate guide is a conductor and connected to an electrode of the plasma source so as to form the primary plasma jet, said primary plasma jet then being transferred to the guide formed of a dielectric material.

* * * * *